United States Patent [19]
Alajem et al.

[11] Patent Number: 5,807,751
[45] Date of Patent: Sep. 15, 1998

[54] APPARATUS AND METHOD FOR DETECTION OF ANALYTES IN A SAMPLE

[75] Inventors: Sara Alajem, Kfar Hanagid; Menachem Ritterband, Nes Ziona; Avraham Reinhartz, Rehovot, all of Israel

[73] Assignee: Gamida Sense Diagnostics Ltd., Ashdod, Israel

[21] Appl. No.: 653,733

[22] Filed: May 23, 1996

[30] Foreign Application Priority Data

May 30, 1995 [IL] Israel ................................. 113920

[51] Int. Cl.$^6$ .......................... C12G 1/68; G01N 33/543
[52] U.S. Cl. ................................. 436/501; 422/58; 435/6; 435/7.92; 435/287.2; 435/288.4; 436/518; 436/809
[58] Field of Search .................. 422/58; 435/6, 435/7.92, 287.2, 288.4; 436/501, 518, 809

[56] References Cited

U.S. PATENT DOCUMENTS

| | | | |
|---|---|---|---|
| 3,552,928 | 1/1971 | Fetter | 422/56 |
| 3,774,455 | 11/1973 | Seidler et al. | 73/444 |
| 3,791,556 | 2/1974 | Tarter | 222/21 |
| 3,791,930 | 2/1974 | Sazholm | 435/30 |
| 4,146,365 | 3/1979 | Kay et al. | 422/57 |
| 4,324,859 | 4/1982 | Saxholm | 435/33 |
| 4,591,556 | 5/1986 | Saxholm | 435/33 |
| 4,594,223 | 6/1986 | Dyke et al. | 422/56 |
| 4,624,929 | 11/1986 | Ullman | 436/179 |
| 4,770,856 | 9/1988 | Uthemann et al. | 422/104 |
| 4,786,594 | 11/1988 | Khanna et al. | 435/7 |
| 4,803,170 | 2/1989 | Stanton et al. | 436/518 |
| 4,847,199 | 7/1989 | Snyder et al. | 435/36 |
| 4,889,816 | 12/1989 | Davis et al. | 436/518 |
| 4,912,034 | 3/1990 | Kalra et al. | 435/7 |
| 4,916,056 | 4/1990 | Brown, III et al. | 435/7 |
| 5,017,341 | 5/1991 | Takekawa | 422/102 |
| 5,084,246 | 1/1992 | Lyman et al. | 422/101 |
| 5,124,129 | 6/1992 | Riccitelli et al. | 422/56 |
| 5,356,785 | 10/1994 | McMahon et al. | 435/7.92 |
| 5,403,551 | 4/1995 | Galloway et al. | 422/58 |

FOREIGN PATENT DOCUMENTS 2147698  5/1985  United Kingdom .

OTHER PUBLICATIONS

L. Olsson et al, Jour. Immunol. Meth., 61, 17–32, 1983.

Primary Examiner—David Saunders
Attorney, Agent, or Firm—Mark M. Friedman

[57] ABSTRACT

Apparatus for detection one or more analyte in a fluid sample. The apparatus includes one or more fluid including the fluid sample to be tested for the analyte(s) and one or more vessels for holding the fluid(s). The vessel includes a base at a first end, side walls extending generally perpendicularly from the base to a second end, an opening in the vessel defined by the side walls and the second end and a central axis extending from the center of the base to the center of vessel opening. The apparatus further includes a single matrix sheet including at least one capture site for capturing a specific analyte which is inserted in vessel and spaced from the central axis opposite the side walls and at least one apparatus for detection of a captured specific analyte.

21 Claims, 2 Drawing Sheets

APPARATUS AND METHOD FOR DETECTION OF ANALYTES IN A SAMPLE

FIELD AND BACKGROUND OF THE INVENTION

The invention relates to a method and apparatus for detection of analytes in a fluid sample.

The use of test devices for detection of analytes is well known in the art. For example, U.S. Pat. No. 4,803,170 to Stanton et al. describes a device for detecting an analyte in a fluid sample including a reaction vessel, and non-overlapping reaction and detection surfaces disposed irreversibly in the vessel. The device described by Stanton et al, however, detects only single analyte in a fluid sample.

SUMMARY OF THE INVENTION

The present invention provides an improved apparatus for detection of analytes in a fluid sample. There is thus provided apparatus for detection of at least one analyte in a fluid sample including at least one fluid including the fluid sample to be tested for the at least one analyte, at least one vessel for holding the at least one fluid including, a base at a first end, side walls extending generally perpendicularly from the base to a second end, an opening in the vessel defined by the side walls and the second end and a central axis extending from the center of the base to the center of the vessel opening, a single matrix sheet including at least one capture site for capturing a specific analyte, inserted in the vessel and spaced from the central axis opposite the side walls, and at least one apparatus for detection of a captured specific analyte. According to a preferred embodiment of the invention the single sheet matrix comprises at least one member.

According to another preferred embodiment of the invention the single sheet matrix comprises a plurality of members. According to yet another preferred embodiment of the invention at least two of the plurality of members at least partially overlap.

According to still another preferred embodiment of the invention the at least one capture site includes at least one capture reagent irreversibly fixed to the at least one capture site. According to a further preferred embodiment of the invention at least a portion of the single matrix sheet is spaced at least 0.001 mm from the base and side walls.

According to yet a further preferred embodiment of the invention the at least one capture site including a plurality of capture sites. According to still a further preferred embodiment of the invention the plurality of capture sites include at least two, at least partially overlapping capture sites.

According to another preferred embodiment of the invention the apparatus for detection analytes in a fluid sample also includes a pipette probe which may be inserted through the opening into the vessel along the central axis to introduce the at least one fluid into the vessel and to remove the at least one fluid from the vessel.

According to yet another preferred embodiment of the invention the at least one apparatus for detection includes a detection reagent which binds to a captured analyte, a fluid containing the detection reagent, and signaling apparatus for signaling the presence of the specific analyte. According to still another preferred embodiment of the invention the signaling apparatus includes a sensible signal bound to the detection reagent. According to a further preferred embodiment of the invention the sensible signal is a color signal.

According to still a further preferred embodiment of the invention the signaling apparatus includes, a developable signal bound to the detection reagent, a developing reagent, and a fluid containing the developing reagent. According to yet a further preferred embodiment of the invention the developable signal is a color signal.

According to another preferred embodiment of the invention the developable signal is retained in the capture site. According to yet another preferred embodiment of the invention the developable signal is contained in the fluid containing the developing reagent.

According to a further preferred embodiment of the invention the capture reagent comprises an antibody.

According to yet a further preferred embodiment of the invention the capture reagent comprises an antigen.

According to still a further preferred embodiment of the invention the capture reagent comprises a DNA sequence.

According to another preferred embodiment of the invention the capture reagent comprises an RNA sequence.

According to yet another preferred embodiment of the invention the detection reagent comprises an antibody.

According to still another preferred embodiment of the invention the detection reagent comprises an antigen.

According to a further preferred embodiment of the invention the detection reagent comprises a DNA sequence.

According to still a further preferred embodiment of the invention the detection reagent comprises an RNA sequence.

According to yet another preferred embodiment of the invention the vessel comprises a generally light transmissive vessel.

According to a further preferred embodiment of the invention the single matrix sheet is removably inserted in the at least one vessel. According to yet a further preferred embodiment of the invention the single matrix sheet is spaced between 0.5 mm and 10. mm from the central axis.

According to still a further preferred embodiment of the invention the single matrix sheet is inserted into a single vessel.

According to another preferred embodiment of the invention the single matrix sheet is inserted into a plurality of vessels.

According to yet another preferred embodiment of the invention the single matrix sheet includes a window opposite the base for light transmission through the light transmissive vessel along the central axis.

There is also provided by the present invention a method for detection of at least one analyte in a fluid sample comprising the steps of, providing a vessel for holding a fluid sample, providing a single matrix sheet inserted in the vessel and spaced from the central axis including a capture site wherein at least one capture for capturing a specific analyte is immobilized to the capture site and, introducing a volume of a fluid sample to be tested for at least one analyte, incubating the fluid sample in the vessel for a predetermined period of time, removing the fluid sample, introducing a volume of a fluid containing a detection reagent which binds the analyte and is conjugated to a color producing enzyme, incubating the fluid containing the detection reagent for a predetermined period of time, removing the fluid containing the detection reagent, introducing a fluid containing a developing reagent wherein a reaction between the developing reagent and the detection reagent produces a visible color reaction in the capture site which is a function of analyte concentration.

BRIEF DESCRIPTION OF THE DRAWINGS

The present invention will be understood and appreciated more fully from the following detailed description taken in conjunction with the drawings in which.

DESCRIPTION OF THE PREFERRED EMBODIMENTS

Reference is now made to FIGS. 1–4 which illustrate apparatus for detection of at least one analyte in a fluid sample constructed and operative in accordance with preferred embodiments of the present invention.

Figure 1:
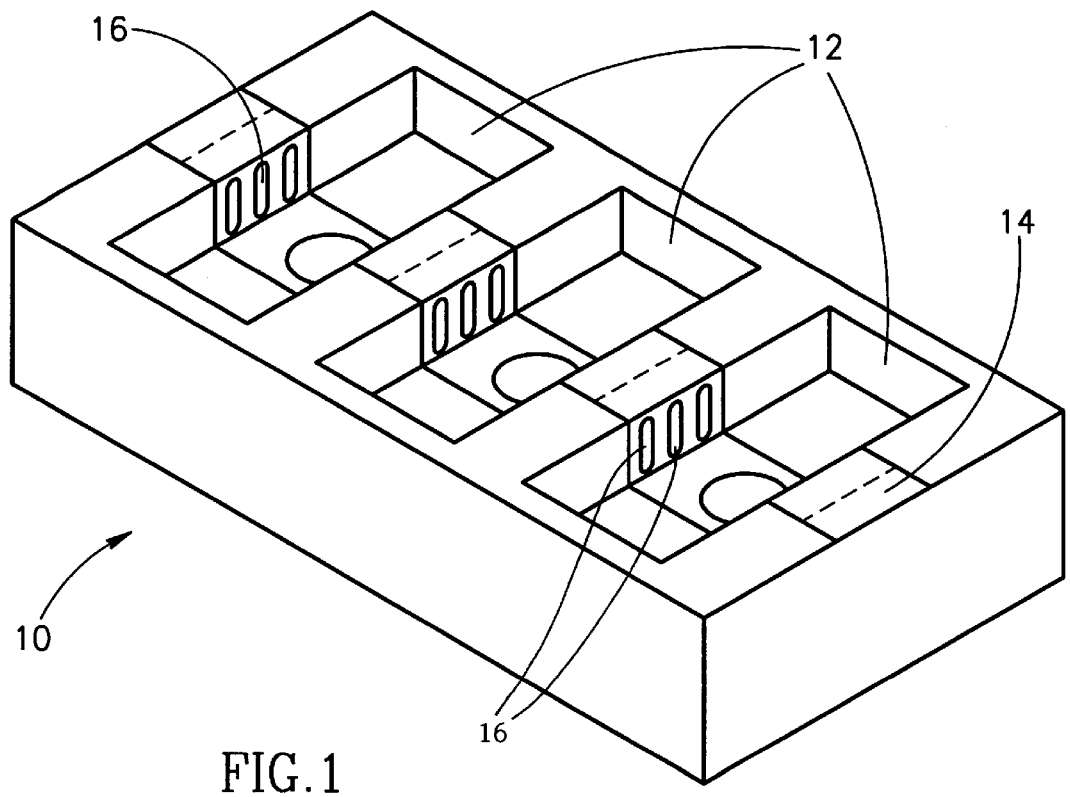
FIG. 1 a pictorial illustration of a preferred embodiment of an apparatus for detection of analytes a fluid sample constructed and operative in accordance with the present invention.

Apparatus 10 includes a single vessel 12 (best seen in FIGS. 3 and 4) or a plurality of vessels (12) (best seen in FIG. 1). A single matrix sheet (14) is disposed in the vessels 12. The single sheet matrix 14 is typically constructed from one or more members each member being fabricated from binding materials such as nitrocellulose, cellulose, nylon or glass fibers.

The single sheet matrix 14 may include members fabricated from one or more materials and includes at least one capture site 16. The single sheet matrix 14 may be fabricated with one or more members overlapping each other and with one or more capture sites 16. The capture sites 16 may also either be separate or at least partially overlap. The matrix sheet 14 is typically planar but is folded along lines 18 (best seen in FIG. 2) to permit insertion of the matrix sheet 14 in the vessels 12. The matrix sheet 14 is typically disposed in vessels 12 spaced between 0.5 mm and 10. mm, preferably between 2.9 mm and 3.1 mm from the central axis 20 and between 0.001 mm and 2.9 mm from a base 22 and side walls 24 of vessels 12. The matrix 14 is preferably removably disposed in the vessels 12, although it may be fixed entirely or partially to the base and walls. The vessels 12 are typically fabricated from polystyrene, and the base 22 and side walls 24 are typically light transmissive.

Figure 5:
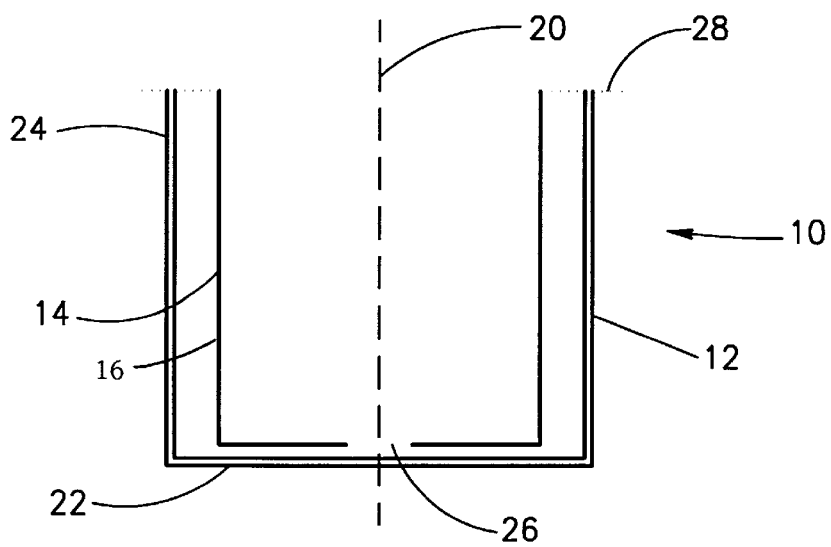
FIG. 5 is yet another embodiment.

The matrix sheet 14 in the area of the base 22 may be formed with a window 26 to allow light to pass through the vessel 12 along the central axis 20. The matrix sheet 14 in the area of the opening in the vessel which defined by the side walls and the second end, may be formed with a gripping area 28 to allow removing the matrix sheet 14 from vessel 12 (best seen in FIG. 5). The matrix sheet 14 in the area of the gripping area 28 may be connected each other in a tearing line 30 to allow separation between the connected matrix sheet 14 during or after pulling the matrix sheets 14 out of vessels 12 within apparatus 10 (best seen in FIG. 2). In the use of apparatus 10, a fluid sample 20 $\mu$l to 1000 $\mu$l which may contain one or more analytes to be detected is disposed in the vessels 12, using a mechanically or manually operated pipette inserted in the vessel along the central axis 20. The sheet matrix 14 including one or more capture sites 16 is disposed in the vessels 12.

Before being inserted in the vessels 12 at least one capture reagent is irreversibly fixed by chemical or physical binding procedures to one or more capture sites 16. The capture reagent is typically an antigen, antibody, RNA or DNA sequence which binds the analyte. The fluid sample is allowed to incubate in the vessel 12 for between 1 min and 24 hours and is then removed by pipette. A volume of fluid of between 20 $\mu$l to 1 ml containing a detection reagent which binds the analyte and which is also bound to a sensible signal is then allowed to incubate in the vessel 12 for between 1 minute and 24 hours.

The detection reagent is typically an antibody, antigen, DNA or RNA sequence. The sensible signal is typically a signal generating compound such as enzymes, colored particles or light emitting substances and is bound to the detection reagent by chemical or physical reactions. The sensible signal may itself be detectable itself as a color change in the capture area as with colored particles or light. The sensible signal, however, may also be a developable signal, typically an enzymatic reaction where a substrate converts a chromogen into a visually detectable signal. If the signal is a developable signal, then fluid containing the detection reagent may be replaced with a 20 $\mu$l to 1 ml of a fluid containing a development reagent such as o-phenylene-diamine.2HCL.

The development reagent produces a sensible reaction such as a color reaction either in the fluid or the at the capture site. The sensible signal may be detected in the vessel by visual observation of the fluid in the vessel or capture site or by using instrumentation for observation of either the fluid or the capture site like spectrophotometer reading for the fluid and scanner reading for the capture site. The sensible signal may also be detected by observation of the sheet matrix after removal of the matrix from the vessels. Reference is now made to the following examples which, together with FIGS. 1–4 illustrate the invention.

EXAMPLE 1

Detection of Human Chorionic Gonadotrophin (HCG)
Preparation of the sheet matrix.

A nitrocellulose (NC) membrane, pore size 0.45 $\mu$m (BioRad, Rockville Center, N.Y., No. 162-0115) is cut into primary sheets 8 cm wide×8 cm long and placed into 5 ml solution containing the following capture reagent, 100 $\mu$g/ml purified IgG1 monoclonal antibody anti-alpha-HCG (Accurate Chemical & Scientific Co., Westbury, N.Y.) in phosphate-buffered saline+0.01% sodium azide (PBSA) at room temperature for 1 hour. The non-specific binding sites are blocked by transferring the membrane to a 250 ml solution containing 10 mg/ml BSA and 0.05% Tween-20 (both from Sigma, St. Louis, Mo., USA), in PBSA and placed for additional incubation for one hour. The membrane is then rinsed briefly with distilled water and allowed to dry at room temperature.

The primary sheet is cut into pieces of 0.4 cm wide/2 cm long to form the sheet matrix comprising the capture reagent. The matrix is inserted into wells of a commercially available microtitration plate (Nunc, Roskilde, Denmark).

Assay Procedure

PBS solution containing the analyte at concentrations of 0, 25, 100, 250 mIU/ml of HCG are tested in replicates in two identical microtitration plates inserted with matrix sheets with the same assay procedure. The assay procedure is performed manually (plate "A"), or using an automated procedure (plate "B").

The assay procedure:

1) addition of 100 $\mu$l sample to a well and incubation for 20 min at room temperature (RT).

2) washing of wells by adding 250 $\mu$l washing solution (0.3% Tween-20 in PBSA) twice.

3) addition of 100 $\mu$l of a solution containing enzyme labeled monoclonal antibody, anti-beta-HCG Horseradish Peroxidase conjugate (1:1000) (Biogenesis Inc., Sandown, N.H.), and incubation for 20 min at RT.

4) washing as in step 2 four times.
5) addition of 200 µl of o-phenylene-diamine .2HCl (OPD) in substrate solution (phosphate-citrate buffer containing hydrogen peroxide), incubation for 20 min at RT.
6) addition of 50 µl of stop solution containing 2N sulfuric acid 7) spectrophotometric reading of plates at 492 nm, for detection of HCG when present in samples, both in manually operated or automated procedures.

EXAMPLE 2

Detection of HCG and test validity control.
Preparation of the sheet matrix:
First member:

A nitrocellulose membrane, pore size 0.45 µm is cut into primary sheets of 8 cm×8 cm and placed into a 5 ml solution containing 100 µg/ml purified IgG1 monoclonal antibody anti-alpha-HCG in PBSA at room temperature for 1 hour. The non-specific binding sites are blocked by transferring the membrane to a 250 ml solution containing 10 mg/ml BSA and 0.05% Tween-20 in PBSA and placed for additional incubation for one hour. The membrane is then rinsed briefly with distilled water and allowed to dry at room temperature. The primary sheet is further cut into pieces 0.4 cm wide×2 cm long to form the first member of the sheet matrix. The first member of the sheet matrix is then placed at the bottom of a microtitration well.
Second member:

A molded ring-shaped cylinder having a thin wall (0.1 mm) and a height of 0.2 cm, consisting of high-impact-polystyrene (HIPS) as a matrix sheet, is placed into a 5 ml solution containing 25 µg/ml purified IgG monoclonal antibody anti-human-hemoglobin in PBSA, at room temperature for 1 hour. The non-specific binding sites are blocked by transferring the HIPS cylinder to a 250 ml solution containing 10 mg/ml BSA and 0.05% Tween-20 in PBSA and placed for an additional incubation of one hour. The HIPS is then rinsed briefly with distilled water and allowed to dry at room temperature. The second member of the matrix sheet is then inserted into the same microtitration well, above the first member, so that both matrix surfaces are in contact.
Assay Procedure:

Diluted serum (1/100) in PBS, with a final concentration of 0, 25, 100, 250 mIU/ml HCG is tested in two identical microtitration plates (A, B). In each plate samples without diluted serum are added as validation controls.
The assay procedure:
1) addition of 150 µl sample to a well and incubation for 20 min at RT.
2) washing of wells by adding 250 µl washing solution (0.3% Tween-20 in PBSA) twice.
3) addition of 150 µl of a solution containing a mixture of enzyme-labelled antibodies, anti-beta-HCG β-galactosidase conjugate, and anti-human-hemoglobin alkaline phosphatase conjugate. Incubation for 20 min at room temperature.
4) washing as in step 2, four times.
Signal development plate A:
5) addition of 250 µl of oNPG substrate solution, o-nitrophenyl-β-D-galactoside in 100 mM Tris HCl pH 7.5, incubation for 30 min at RT.
6) Immediately, spectrophotometric reading of the plate at 420 nm, for detection of HCG when present in the sample.
7) washing as in step 2.
8) addition of 200 µl of BCIP-NBT substrate solution, 5-bromo-4-chloro-3-indolyl phosphate/nitro blue tetrazolium in 100 mM Tris HCl pH 9.5, 5 mM $MgCl_2$ buffer, incubation for 10 min.
9) visual reading of blue/purple precipitated color is retained in unit B, indicates a successful test run.

Signal development plate B:
5) addition of 100 µl of oNPG substrate solution, o-nitrophenyl-β-D-galactoside in 100 mM Tris HCL pH 7.5, incubation for 30 min at RT.
6) addition of 100 µl of PMP substrate solution, phenol-phthalein monophosphate in 100 mM sodium carbonate pH 9.9, 10 MM $MgCl_2$ buffer, incubation for 30 min at RT.
7) addition of 50 µl 0.25N sodium hydroxide.
8) The two developed signals are read spectrophotometrically at 420 nm and 540 nm.

The OD at 420 nm which is obtained for each sample is proportional to the HCG concentrations in the samples. The OD at 540 nm which is obtained for the different samples indicates the validity of the assay for each sample.

EXAMPLE 3

Figure 2:
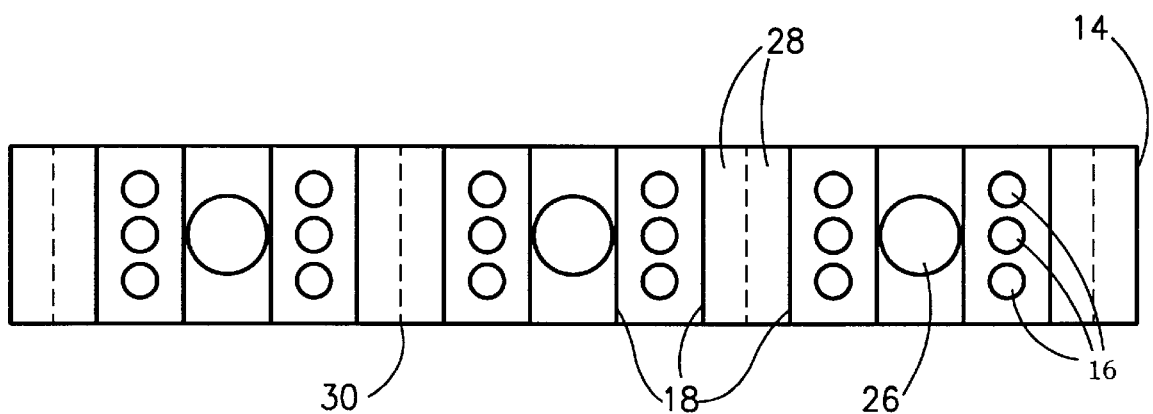
FIG. 2 is a pictorial representation of a portion of the apparatus of FIG. 1.

Detection of specific DNA by hybridization.
Preparation of the sheet matrix:

A nitrocellulose membrane, pore size 0.45 µm, is cut in a pattern similar to that shown in FIG. 2. Three different DNA sequences are immobilized to the matrix sheet at three different capture sites; pBR322 (I); Lambda DNA/Hind III (II); ox 174,RF DNA (III) (Promega, Madison, USA). The DNA sequences, each as a 10 pg/µl solution in 10×SSC, are spotted (1 µl) at intervals of 0.5 cm onto the sheet matrix. The DNAs are fixed to the membrane by baking at 80° C. for 2 hours. The matrix sheet are inserted to microtiter wells.
Sample labeling:

pBR322, Lambda DNA/Hind III, ox 174, RF and a mixture of the three DNAs are labeled by the random primer DNA labeling method with digoxigenin dUTP according to the DIG DNA Labeling Kit protocol Boehringer Biochemica, Mannheim, Germany. The four samples of labeled DNA's are diluted in the hybridization solution according to DIG Nucleic-Acid detection Kit at final concentration of 100 ng/ml. The DNAs are heat denaturated and kept at 4° C.
Hybridization in Formamide solution:

The assay procedure is performed according to the DIG Nucleic-Acid detection Kit.
1) Addition of 150 µl prehybridization solution containing 200 µg/ml salmon sperm DNA (Sigma, St. Louis, USA) to four different wells A,B,C and D, and incubation at 42° C. for 1 hour.
2) discarding of the prehybridization solution and addition of 150 µl of the hybridization solution containing the labeled DNA pBR 322 to well A; Lambda DNA/Hind III to well B; ox 174 rf to well C and the DNA mixture to well D. Incubation for 1 hour at 42° C.
3) Washing in 250 µl of wash solution 1 containing 2×SSC, 0.1% SDS, seven times at RT.
4) Washing in 250 µl of wash solution 2 containing 0.1×SSC, 0.1% SDS, seven times at RT.
5) Washing in 250 µl of wash solution 3 containing 100 mM Tris HCL, 150 mM sodium chloride at pH 7.5 at RT.
6) addition of 150 µl blocking solution and incubation for 30 min at RT.
7) Addition of anti-digoxigenin/alkaline-phosphatase conjugate and incubation for 30 min at RT.
8) Washing as in step 5, four times.
9) Addition of 200 µl of color substrate solution and incubation for 15 min at RT.
10) Washing as in step 8.
11) Removing the matrix sheet from the microtitration wells by grasping the projection (designed for facilitating handling of the matrix) and visually reading the precipitated color.

A visible spot will appear on the capture sites whenever the sample contains homologous DNA.

EXAMPLE 4

Detection of specific antibody

Preparation of the sheet matrix:

The sheet matrix is prepared as described in example 1 except that the capture reagent which is immobilized to the matrix is a specific antigen.

Assay procedure:

A. Sample containing the antibody analyte is incubated with the capture reagent antigen, which is first immobilized on the matrix. The unbound antibody is washed off. The captured antibody is detected by adding to the well solution containing antigen conjugated to alkaline phosphatase (AP), specifically recognizing the antibody. The uncombined conjugate is washed off and a solution containing OPD is added. Spectrophotometric reading of the well at 492 nm, for detection of the presence of the antibody in the sample and its level.

B. The same experiment is repeated, using a gold-labeled conjugate in place of the AP/antigen conjugate. Development of color on the capture sites indicates the presence of antibody in the sample.

EXAMPLE 5

Detection of HCG, with a control test for validation, employing a single-member sheet matrix.

The experiment described in example 2 is repeated using overlapping capture sites located on a single-member matrix sheet.

Preparation of the matrix sheet:

The NC sheet membrane is placed in a solution containing both capture reagents immobilized and inserted into the well.

Assay procedure:

Assay procedure is repeated as described for "plate B" example 2. The OD at 420 nm which is obtained is proportional to the HCG concentration in the samples. The OD at 540 nm which is obtained for the different samples indicates the validity of the assay for each sample.

EXAMPLE 6

Detection of HCG with a control test for validation

Preparation of the matrix sheet:

The first and the second members of the matrix sheet are prepared as described in example 2. The first member, 0.4 cm wide×2 cm long, and the second member, 0.2 cm wide×2 cm long, are glued side by side at a distance of 0.1 cm on a third member of the matrix sheet, a nylon net, 0.7 cm wide×2 cm long.

Assay procedure:

As in example 2.

EXAMPLE 7

Example 1 is repeated except that the matrix sheet is inserted into a flat-bottom tube with a diameter of 0.64 cm and a height of 4 cm. The assay procedure is performed manually as for "plate A" in example 1.

EXAMPLE 8

Figure 3:
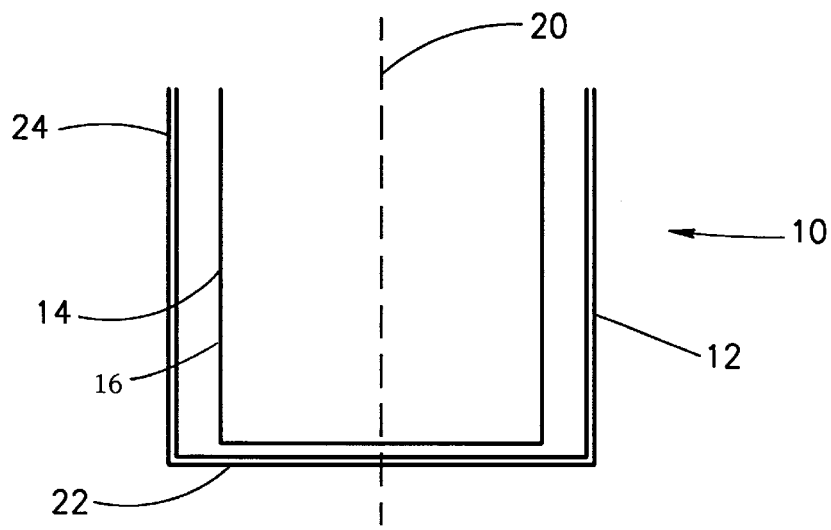
FIG. 3 is a side sectional illustration of another preferred embodiment of the apparatus of FIG. 1.
Figure 4:
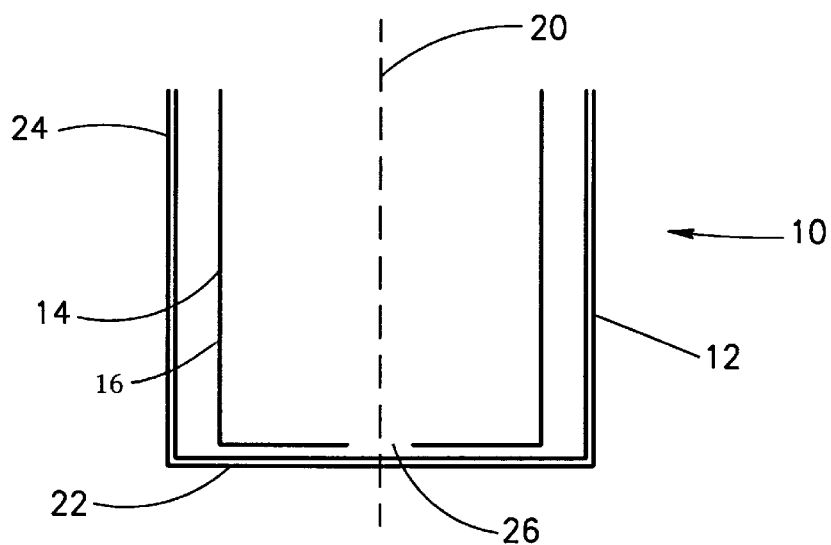
FIG. 4 is a side sectional illustration of yet another preferred embodiment of the apparatus of FIG. 1.

Example 3 is repeated except that the matrix sheet is without the window (26) best shown in FIG. 3.

While the invention has been described with respect to a limited number of embodiments, it will be appreciated that many variations, modifications and other applications of the invention may be made.

What is claimed is:

1. An apparatus for detecting an analyte in a fluid sample, the apparatus comprising:

(a) a vessel for holding the fluid sample, said vessel including a base at a first end, said vessel further including side walls extending from said base to a second end, thereby defining an opening in said vessel, said base and opening defining an axis extending from said base to said opening; and (b) a matrix sheet including a capture site for capturing the analyte, said matrix sheet being disposed in said vessel close to said walls and spaced from said axis;

wherein at least a portion of said matrix sheet is disposed more than 0.001 mm and less than 2.9 mm from said side walls, such that the fluid sample is present on both sides of said matrix sheet and further such that said matrix sheet permits microtitration via said opening.

2. The apparatus of claim 1, wherein at least a portion of said base is light transmissive for allowing passage of light through said base along said axis and through said opening.

3. The apparatus of claim 1, wherein at least another portion of said matrix sheet is disposed more than 0.001 mm and less than 2.9 mm from said base, such that the fluid sample is present on both sides of said matrix sheet.

4. The apparatus of claim 1, further comprising a nylon net being disposed between said walls and said matrix sheet for effecting said disposition of more than 0.001 mm and less than 2.9 mm of said matrix sheet and said side walls.

5. The apparatus of claim 1, wherein said vessel is a part of a microtitration plate.

6. The apparatus of claim 1, wherein said capture site includes at least one capture reagent irreversibly fixed to said matrix sheet at said capture site.

7. The apparatus of claim 1, wherein said matrix sheet includes a plurality of capture sites.

8. The apparatus of claim 7, wherein said plurality of capture sites includes at least two, at least partially overlapping capture sites.

9. The apparatus of claim 8, wherein said capture reagent includes a moiety selected from the group consisting of an antibody, an antigen, a DNA sequence and an RNA sequence.

10. The apparatus of claim 1, wherein said matrix sheet is removably inserted in said vessel.

11. The apparatus of claim 1, wherein said matrix sheet is spaced between 0.5 mm and 10 mm from said axis.

12. The apparatus of claim 1, wherein said matrix sheet is formed with a window, said window is positioned opposite said base and effects said light transmission along said axis.

13. The apparatus of claim 1 wherein said axis is a central axis.

14. An apparatus for detecting analytes in fluid samples contained in vessels of a multititration plate, each of the vessels serves for holding a single fluid sample, each of the vessels including a base at a first end, at least a portion of said base being light transmissive, each of the vessels further including side walls extending from the base thereof to a second end, thereby defining an opening in each of said vessels, the base and opening of each of the vessels defining an axis extending from the respective base to the respective opening, the apparatus comprising a foldable matrix sheet including capture sites for capturing the analytes, said matrix sheet being formed with windows, said windows being spaced from one another such that when said sheet is folded and disposed in the vessels, said windows are positioned opposite said bases and serve for effecting light transmission along the axes of the vessels, said capture sites being spaced from one another such that when said sheet is folded and disposed in the vessels, said capture sites are positioned within said vessels, for effecting the capturing of the analytes in the fluid sample.

15. The apparatus of claim 14, wherein each of said capture sites includes at least one capture reagent irreversibly fixed to said matrix sheet at said capture site.

16. The apparatus of claim 14, wherein said matrix sheet includes a plurality of different capture sites.

17. The apparatus of claim 16, wherein said plurality of different capture sites includes at least two, at least partially overlapping different capture sites.

18. The apparatus of claim 15, wherein said capture reagent includes a moiety selected from the group consisting of an antibody, an antigen, a DNA sequence and an RNA sequence.

19. The apparatus of claim 14, wherein said axis is a central axis.

20. A method for detection of an analyte in a fluid sample comprising the steps of:
   (a) providing a vessel for holding the fluid sample, said vessel including a base at a first end and side walls extending from said base to a second end, thereby defining an opening in said vessel, said base and opening defining an axis extending from said base to said opening;
   (b) providing a matrix sheet including a capture site for capturing the analyte;
   (c) inserting said matrix sheet into said vessel, such that said sheet is disposed close to said walls and spaced from said axis, wherein at least a portion of said matrix sheet is disposed more than 0.001 mm and less than 2.9 mm from said side walls, such that the fluid sample will be present on both sides of said matrix sheet;
   (d) introducing a volume of the fluid sample to be tested into said vessel, such that the capture site is contacted with the fluid sample;
   (e) incubating the fluid sample in said vessel;
   (f) removing the fluid sample from said vessel;
   (g) introducing into said vessel a volume of a fluid containing a colorimetric detection reagent capable of binding the analyte; and
   (h) incubating said fluid containing said detection reagent in said vessel, in the presence of said matrix sheet.

21. The method of claim 20, wherein said axis is a central axis.

* * * * *